(12) United States Patent
Kibino et al.

(10) Patent No.: US 7,754,926 B2
(45) Date of Patent: Jul. 13, 2010

(54) PRODUCTION PROCESS OF 3-ALKOXY-1-PROPANOLS, AND 3-ALKOXY-1-PROPANOLS OBTAINED BY THE PRODUCTION PROCESS

(75) Inventors: Nobuyuki Kibino, Oita (JP); Yasushi Kadowaki, Oita (JP); Masaaki Sakai, Oita (JP); Yukiharu Hetsugi, Oita (JP)

(73) Assignee: Showa Denko K.K., Tokyo (JP)

( * ) Notice: Subject to any disclaimer, the term of this patent is extended or adjusted under 35 U.S.C. 154(b) by 952 days.

(21) Appl. No.: 10/588,085

(22) PCT Filed: Feb. 4, 2005

(86) PCT No.: PCT/JP2005/002089
§ 371 (c)(1),
(2), (4) Date: Jul. 31, 2006

(87) PCT Pub. No.: WO2005/075392
PCT Pub. Date: Aug. 18, 2005

(65) Prior Publication Data
US 2007/0161828 A1    Jul. 12, 2007

Related U.S. Application Data

(60) Provisional application No. 60/543,294, filed on Feb. 11, 2004, provisional application No. 60/543,405, filed on Feb. 11, 2004.

(30) Foreign Application Priority Data

Feb. 5, 2004   (JP) .............................. 2004-028732
Feb. 5, 2004   (JP) .............................. 2004-028733

(51) Int. Cl.
C07C 41/18   (2006.01)
C07C 29/10   (2006.01)

(52) U.S. Cl. ..................... 568/678; 568/865; 568/866

(58) Field of Classification Search ................. 568/866
See application file for complete search history.

(56) References Cited

U.S. PATENT DOCUMENTS

2004/0147756 A1 * 7/2004 Miyata et al. ............ 546/281.7

FOREIGN PATENT DOCUMENTS

EP      1 201 633 A1    5/2002
JP      56-138125 A    10/1981

OTHER PUBLICATIONS

Yamakawa et al., 2 Catal. Comm. 191-94 (2001).*
Berkessel et al.,254 Appl. Catl. A, 27-34 (2003).*
Kobayashi et al., 72 Pure Appl. Chem., 1373-80 (2000).*
Tetsu Yamakawa, et al, "Selective Synthesis of 3-Methoxy-1-Propanol From Methanol and Allyl Alcohol With Metal Oxide Catalysts", Catalysis Communications, vol. 2, 2001, pp. 191-194, XP002331426.
Tetsu Yamakawa, et al, "Synthesis of 3-Alkoxy-1-Propanol From Allyl Alcohol by Use of Metal Oxide Catalysts in the Liquid-Phase", Science and Technology in Catalysis 2002, 2003, pp. 549-550, XP008048324.
Database CA 'Online!, Chemical Abstracts Service, Columbus, Ohio, US; "Hydrolysis of Mono-Tertiary-Alkyl Ethers of Alkylene Glycols", XP002341169, Retrieved From STN, Database Accession No. 1982-85044, Abstract, (1982).

* cited by examiner

*Primary Examiner*—Brian J Davis
(74) *Attorney, Agent, or Firm*—Sughrue Mion, PLLC

(57) ABSTRACT

The present invention reacts an allyl alcohol with an alcohol compound in the presence of a catalyst containing at least one element selected from the group consisting of elements of the group III, lanthanoid elements and actinoid elements of the Periodic Table, as depicted in the following reaction

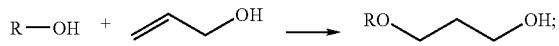

and provides a method for efficiently producing 3-alkoxy-1-propanol in a single step using an alcohol as a starting material.

13 Claims, No Drawings

PRODUCTION PROCESS OF 3-ALKOXY-1-PROPANOLS, AND 3-ALKOXY-1-PROPANOLS OBTAINED BY THE PRODUCTION PROCESS

CROSS REFERENCE TO RELATED APPLICATIONS

This application is a 371 of PCT/JP2005/002089, filed Feb. 4, 2005, and claims the priority of application based on U.S. Provisional Application Ser. No. 60/543,294 (filed on Feb. 11, 2004) and U.S. Provisional Application Ser. No. 60/543,405 (filed on Feb. 11, 2004).

BRIEF SUMMARY OF THE INVENTION

The present invention relates to a method for producing 3-alkoxy-1-propanols, and 3-alkoxy-1-propanols produced by the method and derivatives thereof. More particularly, it relates to a method for producing 3-alkoxy-1-propanols and derivatives thereof, which comprises using an allyl alcohol as a starting material.

BACKGROUND OF THE INVENTION 3-alkoxy-1-propanols have a hydroxyl group in the molecule and can be used as materials for various reactions such as esterification reaction, etherification reaction and halogenation reaction, and are therefore important compounds suited for use as materials for many useful compounds, especially intermediates for medicines and agrochemicals, silane coupling agents and polyester modifiers. Also 3-alkoxy-1-propanols are useful compounds because 1,3-propanediol as a material of polytrimethylene terephthalate, which has become of major interest recently, can be derived therefrom when the alkoxy ether moiety is hydrolyzed.

Japanese Unexamined Patent Publication (Kokai) No. 10-306,050 discloses, as a method for producing 3-alkoxy-1-propanol, a method for producing 3-alkoxy-1-propanol, which comprises hydrogenating 3-alkoxy-1-propanal produced by reacting an alcohol with acrolein.

However, this method had such a problem that 3-alkoxy-1-propanal as an intermediate product and acrolein as a material may cause a secondary reaction because of good reactivity to produce a large amount of by-products, and also the production process requires two steps, resulting in a complicated process.

Japanese Unexamined Patent Publication (Kokai) No. 8-113,546 discloses a method for producing 3-alkoxy-1-propanol, which comprises using an alkoxide of an alkali metal, and a halide. However, this method also had such a problem that the halide and the alkoxide of the alkali metal used in the reaction must be separately produced, and thus the process requires at least two steps, resulting in high cost for industrial production.

Japanese Unexamined Patent Publication (Kokai) No. 13-247,503 discloses, as a method for solving a problem that the production process requires a lot of steps, a method for producing 3-alkoxy-1-propanol from an alcohol and allyl alcohols in a single step.

This method is an excellent method in that 3-alkoxy-1-propanol can be produced in a single step, however, it is not suited for industrial production because of low catalytic activity.

As described above, there has never been proposed a method for producing 3-alkoxy-1-propanol in a first step in the reaction yield suited for industrial production.

Background associated with 1,3-propanediol as one of derivatives of the above-mentioned 3-alkoxy-1-propanol will now be described.

There has been developed a low-cost method for producing 1,3-propanediol, namely, compounds which are in great latent demand for materials of synthetic resins, especially materials of polyester fibers, using a chemical method or a biological method.

As a chemical method for producing 1,3-propanediol, for example, there have conventionally been known a method for producing 1,3-propanediol, which comprises synthesizing 3-hydroxypropionaldehyde (hereinafter abbreviated to "3-HPA") by the hydration reaction of acrolein, followed by the hydrogenation reaction (Japanese Unexamined Patent Publication (Kokai) No. 10-212,253) and a method for producing 1,3-propanediol, which comprises synthesizing 3-HPA by the hydroformylation reaction of ethylene oxide, followed by the hydrogenation reaction (Kohyo (National Publication of Translated Version) No. 11-515021).

These conventional methods have such a problem that 1,3-propanediol is produced by finally hydrogenating 3-HPA, and thus the unreacted 3-HPA may be remained in 1,3-propanediol. Also there is such a problem that odor and discoloration are caused when a polyester is synthesized by using 1,3-propanediol containing a carbonyl compound such as 3-HPA.

Therefore, it is preferred that the resulting product 1,3-propanediol does not contain a carbonyl compound such as 3-HPA. Japanese Unexamined Patent Publication (Kokai) No. 6-40,973 and Kohyo (National Publication of Translated Version) No. 11-509,828 disclose that it is difficult to remove the carbonyl compound by a conventional purification method such as distillation.

To obtain 1,3-propanediol having a low content of the carbonyl compound including 3-HPA, Japanese Unexamined Patent Publication (Kokai) No. 6-40,973 discloses a method of carrying out the hydrogenation reaction of 3-HPA in two steps and Kohyo (National Publication of Translated Version) No. 11-509,828 discloses a method of removing a carbonyl compound by reacting with an alkali. However, according to both methods, it is difficult to attain 100% of a conversion ratio of 3-HPA, and the remained carbonyl compound must be removed, and this increases a burden to the process, resulting in high production cost.

To solve these problems, a chemical method for producing 1,3-propanediol without using 3-HPA as a material has been studied. The method includes a method of hydrolyzing an ether alcohol compound, namely, 3-alkoxy-1-propanol.

Japanese Unexamined Patent Publication (Kokai) No. 6-157,378 discloses, as a reaction method for producing a diol compound by hydrolyzing an ether alcohol compound such as 3-alkoxy-1-propanol, a method of hydrolyzing 4-oxa-1,7-heptanediol in the presence of a catalyst such as ion-exchange resin or zeolite to obtain 1,3-propanediol.

However, in this publication, a substrate used for hydrolysis is limited to 4-oxa-1,7-heptanediol and it is not disclosed whether or not this method can be applied to the ether alcohol compound. This method had such a problem that high temperature of 200° C. or higher is required for efficient proceeding of the hydrolysis reaction, resulting in high energy cost for industrial production.

Similarly, Japanese Unexamined Patent Publication (Kokai) No. 11-209,318 discloses a method of hydrolyzing an ether compound in the presence of an acid catalyst to obtain an alcohol.

However, this method described in the publication has such a problem that a large amount of by-products other than the alcohol are produced, although a high conversion ratio of the ether compound is attained during the reaction. Also it is difficult to use the method for industrial purposes because of a low selectivity coefficient. Similarly to the above-mentioned method, this method had such a problem that high temperature of 200° C. or higher is required for efficient proceeding of the hydrolysis reaction, resulting in high cost for industrial production.

European Patent No. 1,201,633 also discloses a method of hydrolyzing an ether compound in the presence of an acid catalyst to obtain an alcohol.

However, the method described in the publication also had such a problem that the reaction temperature of 250° C. or higher is required to attain high reaction yield, resulting in high energy cost for industrial production. In this publication, a substrate used for hydrolysis is limited to 4-oxa-1,7-heptanediol and it is not disclosed whether or not this method can be applied to the ether alcohol compound.

As described above, there has never been proposed a method for efficiently producing the objective 1,3-propanediol with low energy by hydrolyzing an ether alcohol compound such as 3-alkoxy-1-propanol.

Patent Document 1: Japanese Unexamined Patent Publication (Kokai) No. 10-306,050

Patent Document 2: Japanese Unexamined Patent Publication (Kokai) No. 13-247,503

Patent Document 3: Japanese Unexamined Patent Publication (Kokai) No. 10-212253

Patent Document 4: Kohyo (National Publication of Translated Version) No. 11-515,021

Patent Document 5: Japanese Unexamined Patent Publication (Kokai) No. 6-40973

Patent Document 6: Kohyo (National Publication of Translated Version) No. 11-509,828

Patent Document 7: Japanese Unexamined Patent Publication (Kokai) No. 6-157,378

Patent Document 8: Japanese Unexamined Patent Publication (Kokai) No. 11-209318

Patent Document 9: European Patent No. 1,201,633

DETAILED DESCRIPTION OF THE INVENTION

An object of the present invention is to provide a method for producing 3-alkoxy-1-propanol and derivatives thereof, which can solve the above-mentioned problems of the prior art.

Another object of the present invention is to provide a method for efficiently producing 3-alkoxy-1-propanol and derivatives thereof in a single step using an allyl alcohol as a starting material, and 3-alkoxy-1-propanol and derivative thereof produced by the method.

As a result of earnest study, the present inventors have found that 3-alkoxy-1-propanol can be efficiently produced by using a catalyst containing specific elements in the case of producing 3-alkoxy-1-propanol from an allyl alcohol and an alcohol compound.

The present invention (I) is directed to a method for producing 3-alkoxy-1-propanols, which comprises reacting an allyl alcohol with an alcohol compound in the presence of at least one catalyst containing at least one element selected from the group consisting of elements of the group III, lanthanoid elements and actinoid elements of the Periodic Table.

The present invention (II) is directed to 3-alkoxy-1-propanols produced by the method for producing 3-alkoxy-1-propanols of the present invention (I).

Furthermore, the present invention includes the following embodiments:

[1] A method for producing 3-alkoxy-1-propanol, which comprises reacting an allyl alcohol with an alcohol compound in the presence of a catalyst containing at least one element selected from the group consisting of elements of the group III, lanthanoid elements and actinoid elements of the Periodic Table.

[2] The method for producing 3-alkoxy-1-propanol according to [1], wherein the catalyst containing at least one element selected from the group consisting of elements of the group III, lanthanoid elements and actinoid elements of the Periodic Table is an oxide.

[3] The method for producing 3-alkoxy-1-propanol according to [2], wherein the catalyst containing at least one element selected from the group consisting of elements of the group III, lanthanoid elements and actinoid elements of the Periodic Table is selected from the group consisting of scandium oxide, yttrium oxide, lanthanum oxide, samarium oxide, ytterbium oxide, neodymium oxide and lutetium oxide.

[4] The method for producing 3-alkoxy-1-propanol according to [1], wherein the catalyst containing at least one element selected from the group consisting of elements of the group III, lanthanoid elements and actinoid elements of the Periodic Table is an alkoxide compound.

[5] The method for producing 3-alkoxy-1-propanol according to [4], wherein the catalyst containing at least one element selected from the group consisting of elements of the group III, lanthanoid elements and actinoid elements of the Periodic Table is selected from the group consisting of scandium trimethoxide, scandium triethoxide, scandium triisopropoxide, yttrium trimethoxide, yttrium triethoxide, yttrium triisopropoxide, ytterbium trimethoxide, ytterbium triethoxide and ytterbium triisopropoxide.

[6] The method for producing 3-alkoxy-1-propanol according to any one of [1] to [5], wherein the catalyst containing at least one element selected from the group consisting of elements of the group III, lanthanoid elements and actinoid elements of the Periodic Table is supported on a carrier.

[7] The method for producing 3-alkoxy-1-propanol according to [6], wherein the carrier is either activated carbon or magnesia.

[8] The method for producing 3-alkoxy-1-propanol according to [7], wherein a specific surface area of the carrier is 1000 m$^2$/g or more.

[9] The method for producing 3-alkoxy-1-propanol according to any one of [1] to [8], wherein the reaction of the allyl alcohol and the alcohol compound is carried out by a gas phase method.

[10] The method for producing 3-alkoxy-1-propanol according to any one of [1] to [9], wherein the alcohol compound to be reacted with the allyl alcohol is at least one selected from the group consisting of methanol, ethanol, n-propanol, isopropanol, n-butanol, isobutanol, t-butanol, allyl alcohol, phenol and benzyl alcohol.

[11] The method for producing 3-alkoxy-1-propanol according to any one of [1] to [10], wherein the reaction of the allyl alcohol and the alcohol compound is carried out in the presence of water.

[12] The method for producing 3-alkoxy-1-propanol according to [11], wherein the amount of water present in the reaction system is not less than the number of moles of elements in the catalyst containing at least one element selected from the group consisting of elements of the group III, lanthanoid elements and actinoid elements of the Periodic Table.

[13] The method for producing 3-alkoxy-1-propanol according to any one of [1] to [12], wherein a conversion ratio of the allyl alcohol is 20% or more.

[14] The method for producing 3-alkoxy-1-propanol according to any one of [1] to [13], wherein a selectivity coefficient of 3-alkoxy-1-propanol is 60% or more.

[15] The method for producing 3-alkoxy-1-propanol according to any one of [1] to [14], wherein the yield of 3-alkoxy-1-propanol is 0.5 or more per 1 mmol of metal used as the catalyst per one hour of the reaction time; and

[16] 3-alkoxy-1-propanol produced by the method according to any one of [1] to [15].

As a result of further study on the aforementioned 3-alkoxy-1-propanol, the present inventors have found that 1,3-propanediol can be efficiently produced by reacting under mild conditions at a temperature of lower than 200° C. using an acid catalyst in case of producing 1,3-propanediol from an ether alcohol compound having a specific structure, and thus the present invention has been completed.

That is, the present invention (2-I) is directed to a method for producing 1,3-propanediol, which comprises hydrolyzing an ether alcohol compound represented by the general formula (1) at a temperature of lower than 200° C. in the presence of at least one acid catalyst:

General Formula (1)

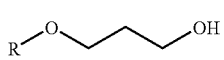

(Chemical Formula 1)

The present invention (2-II) is directed to 1,3-propanediol produced by the method of the present invention (2-I).

Furthermore, the present invention includes the followings:

[2-1] A method for producing 1,3-propanediol, which comprises hydrolyzing an ether alcohol compound represented by the general formula (1) at a temperature of lower than 200° C. in the presence of at least one acid catalyst:

General Formula (1)

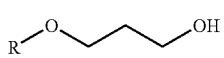

(Chemical Formula 2)

wherein R represents an alkyl group having 1 to 10 carbon atoms, a cycloalkyl group, or an aryl group, provided that R has no hydroxyl group.

[2-2] The method for producing 1,3-propanediol according to [2-1], wherein the acid catalyst is a mineral acid.

[2-3] The method for producing 1,3-propanediol according to [2-1], wherein the acid catalyst is an inorganic solid acid.

[2-4] The method for producing 1,3-propanediol according to [2-1], wherein the acid catalyst is a compound having a sulfonic acid group.

[2-5] The method for producing 1,3-propanediol according to [2-4], wherein the compound having a sulfonic acid group is at least one selected from the group consisting of methanesulfonic acid, trifluoromethanesulfonic acid, p-toluenesulfonic acid, dodecylbenzenesulfonic acid and sulfonic acid type ion-exchange resin.

[2-6] The method for producing 1,3-propanediol according to any one of [2-1] to [2-5], wherein the acid catalyst is soluble in the reaction system and the reaction occurs in a homogeneous state.

[2-7] The method for producing 1,3-propanediol according to any one of [2-1] to [2-5], wherein the acid catalyst is insoluble in the reaction system and the reaction occurs in a heterogeneous state.

[2-8] The method for producing 1,3-propanediol according to any one of [2-1] to [2-7], wherein at least one compound selected from the group consisting of sodium iodide, potassium iodide, hydroiodic acid and tetraalkylammonium iodides is used as an reaction auxiliary.

[2-9] The method for producing 1,3-propanediol according to any one of [2-1] to [2-8], wherein the substituent R of the ether alcohol compound represented by the general formula (1) is a hydrocarbon having 7 or less carbon atoms.

[2-10] The method for producing 1,3-propanediol according to any one of [2-1] to [2-8], wherein the ether alcohol compound represented by the general formula (1) is at least one selected from the group consisting of 3-methoxy-1-propanol, 3-ethoxy-1-propanol, 3-propoxy-1-propanol, 3-allyloxy-1-propanol and 3-benzyloxy-1-propanol.

[2-11] The method for producing 1,3-propanediol according to any one of [2-1] to [2-10], wherein the ether alcohol compound represented by the general formula (1) is produced by reacting an allyl alcohol with an alcohol compound.

[2-12] The method for producing 1,3-propanediol according to any one of [2-1] to [2-11], wherein the hydrolysis reaction is carried out in the presence of water, the mass of which is not more than 5 times the mass of the ether alcohol compound.

[2-13] The method for producing 1,3-propanediol according to any one of [2-1] to [2-12], wherein a conversion ratio of 3-alkoxy-1-propanol is 50% or more.

[2-14] The method for producing 1,3-propanediol according to any one of [2-1] to [2-13], wherein a selectivity coefficient of 1,3-propanediol is 60% or more.

[2-15] 1,3-propanediol produced by the method according to any one of [2-1] to [2-14].

It is apparent that, in the above-mentioned method for producing 1,3-propanediol, when 3-alkoxy-1-propanol obtained by the above-mentioned method is used as an ether alcohol compound of the general formula (1), as a raw material, 1,3-propanediol having a very small content of a carbonyl compound can be obtained, and a resin with less odor and coloration can be produced at a low cost by using the resulting 1,3-propanediol as a material in a resin such as polyester.

BEST MODE FOR CARRYING OUT THE INVENTION

The present invention will now be described in more detail. In the following descriptions, parts and percentages are by mass unless otherwise specified.

(Present Invention (I))

First, the present invention (I) will be described. The present invention (I) is directed to a method for producing 3-alkoxy-1-propanols, which comprises reacting an allyl alcohol with an alcohol compound in the presence of a catalyst containing at least one element selected from the group consisting of elements of the group III, lanthanoid elements and actinoid elements of the Periodic Table.

(Catalyst)

The catalyst used in the method of the present invention (I) is characterized in that it contains at least one element selected from the group consisting of elements of the group III, lanthanoid elements and actinoid elements of the Periodic Table. The catalyst may further contain any element or compound as far as it does not inhibit the reaction of the allyl alcohol and the alcohol compound.

The catalyst used in the method of the present invention (I) is preferably an oxide, hydroxide or alkoxide, preferably an oxide, hydroxide or alkoxide of elements of group III of the Periodic Table, lanthanoid elements or actinoid elements.

(Oxide)

Oxides such as scandium oxide, yttrium oxide, lanthanum oxide, cerium oxide, praseodymium oxide, neodymium oxide, samarium oxide, europium oxide, gadolinium oxide, dysprosium oxide, holmium oxide, erbium oxide, ytterbium oxide, lutetium oxide, actinium oxide and thorium oxide can be used as the catalyst.

Among these oxides, scandium oxide, yttrium oxide, lanthanum oxide, praseodymium oxide, samarium oxide, gadolinium oxide, dysprosium oxide, holmium oxide, erbium oxide and ytterbium oxide are preferable, and scandium oxide, yttrium oxide and ytterbium oxide are more preferable.

(Hydroxide)

Hydroxides such as scandium hydroxide, yttrium hydroxide, lanthanum hydroxide, cerium hydroxide, praseodymium hydroxide, neodymium hydroxide, samarium hydroxide, europium hydroxide, gadolinium hydroxide, dysprosium hydroxide, holmium hydroxide, erbium hydroxide, ytterbium hydroxide, lutetium hydroxide, actinium hydroxide and thorium hydroxide can be used as the catalyst.

Among these hydroxides, scandium hydroxide, yttrium hydroxide, lanthanum hydroxide, praseodymium hydroxide, samarium hydroxide, gadolinium hydroxide, dysprosium hydroxide, holmium hydroxide, erbium hydroxide and ytterbium hydroxide are preferable, and scandium hydroxide, yttrium hydroxide and ytterbium hydroxide are more preferable.

(Alkoxide)

Alkoxides such as scandium trimethoxide, scandium triethoxide, scandium triisopropoxide, yttrium trimethoxide, yttrium triethoxide, yttrium triisopropoxide, lanthanum trimethoxide, lanthanum triethoxide, lanthanum triisopropoxide, praseodymium trimethoxide, praseodymium triethoxide, praseodymium triisopropoxide, samarium trimethoxide, samarium triethoxide, samarium triisopropoxide, gadolinium trimethoxide, gadolinium triethoxide, gadolinium triisopropoxide, dysprosium trimethoxide, dysprosium triethoxide, dysprosium triisopropoxide, holmium trimethoxide, holmium triethoxide, holmium triisopropoxide, erbium trimethoxide, erbium triethoxide, erbium triisopropoxide, ytterbium trimethoxide, ytterbium triethoxide and ytterbium triisopropoxide can be used as the catalyst.

Among these alkoxides, scandium trimethoxide, scandium triethoxide, scandium triisopropoxide, yttrium trimethoxide, yttrium triethoxide, yttrium triisopropoxide, samarium trimethoxide, samarium triethoxide, samarium triisopropoxide, ytterbium trimethoxide, ytterbium triethoxide and ytterbium triisopropoxide are preferable, and scandium trimethoxide, scandium triethoxide, scandium triisopropoxide, yttrium trimethoxide, yttrium triethoxide and yttrium triisopropoxide are more preferable.

(Form of Catalyst)

The form of the catalyst used in the method of the present invention (I) is not specifically limited and may be in either a homogeneous form or a heterogeneous form. The catalyst is preferably a heterogeneous catalyst in view of the operation for separation of the catalyst after the completion of the reaction, but may be a homogeneous catalyst.

Any homogeneous catalyst can be used as far as it is soluble during the reaction.

The homogeneous catalyst may be used in the reaction in the form of being dissolved previously in substrates such as allyl alcohol and an alcohol compound, or may be used in the reaction by charging simultaneously with the substrate.

Any heterogeneous catalyst can be used as far as it is insoluble during the reaction. For example, there can also be used a so-called supported type catalyst comprising a carrier and a component supported on the carrier, the component containing at least one element selected from the group consisting of elements of the group III, lanthanoid elements and actinoid elements of the Periodic Table.

(Supported Type Catalyst)

When the catalyst used in the method of the present invention (I) is a supported type catalyst comprising a carrier and a catalyst supported on the carrier, usable carrier is not specifically limited as far as it does not react with the component containing at least one element selected from the group consisting of elements of the group III, lanthanoid elements and actinoid elements of the Periodic Table. Conventionally known carriers can be used. To exhibit catalytic activity, the carrier must not react with the component containing at least one element selected from the group consisting of elements of group III, lanthanoid elements and actinoid elements of the Periodic Table under conditions for production of the catalyst. A carrier which reacts with the component to form a complex oxide after the completion of the production of the catalyst is not preferable.

(Carrier)

As the carrier, for example, activated carbon and magnesia can be used. In view of the influence on the reaction, the specific surface area during the production of the catalyst, or industrial utility such as strength of the carrier, activated carbon is preferable.

The surface area of the carrier which is used in the catalyst used in the method of the present invention (I) is preferably within a range from 100 to 4000 m$^2$/g, more preferably from 300 to 4000 m$^2$/g, and still more preferably from 700 to 4000 m$^2$/g.

When the component containing, as active species of the catalyst, at least one element selected from the group consisting of elements of the group III, lanthanoid elements and actinoid elements of the Periodic Table is supported on the carrier, the amount of the component containing elements is preferably from 0.01 to 100% by mass based on the total mass of the carrier. When the amount of the component containing elements is less than 0.01% by mass, sufficient catalytic activity suited for practical use may not be obtained because of a low concentration of a catalytic active site, and therefore it is not preferable. On the other hand, when the amount exceeds 100% by mass, the effect of the carrier may not be exerted, and therefore it is not preferable.

The amount is more preferably within a range from 0.05 to 50% by mass, and still more preferably from 0.1 to 30% by mass.

(Preferred Combination of Supported Type Catalysts)

When the catalyst used in the method of the present invention (I) is a supported type catalyst comprising a carrier and a catalyst supported on the carrier, there can be used, for example, scandium oxide-activated carbon, scandium oxide-magnesia, yttrium oxide-activated carbon, yttrium oxide-magnesia, lanthanum oxide-activated carbon, lanthanum oxide-magnesia, praseodymium oxide-activated carbon, praseodymium oxide-magnesia, samarium oxide-activated carbon, samarium oxide-magnesia, gadolinium oxide-activated carbon, gadolinium oxide-magnesia, dysprosium oxide-activated carbon, dysprosium oxide-magnesia, holmium oxide-activated carbon, holmium oxide-magnesia, erbium oxide-activated carbon, erbium oxide-magnesia, ytterbium oxide-activated carbon, ytterbium oxide-magnesia, scandium trimethoxide-activated carbon, scandium trimethoxide-magnesia, scandium triethoxide-activated carbon, scandium triethoxide-magnesia, scandium triisopropoxide-activated carbon, scandium triisopropoxide-magnesia, yttrium trimethoxide-activated carbon, yttrium trimethoxide-magnesia, yttrium triethoxide-activated carbon, yttrium triethoxide-magnesia, yttrium triisopropoxide-activated carbon, yttrium triisopropoxide-magnesia, samarium trimethoxide-activated carbon, samarium trimethoxide-magnesia, samarium triethoxide-activated carbon, samarium triethoxide-magnesia, samarium triisopropoxide-activated carbon, samarium triisopropoxide-magnesia, ytterbium trimethoxide-activated carbon, ytterbium trimethoxide-magnesia, ytterbium triethoxide-activated carbon, ytterbium triethoxide-magnesia, ytterbium triisopropoxide-activated carbon and ytterbium triisopropoxide-magnesia. These catalysts may be used alone or in combination.

When the catalyst used in the method of the present invention (I) is a heterogeneous catalyst, a supported type catalyst containing at least one element selected from the group consisting of elements of the group III, lanthanoid elements and actinoid elements of the Periodic Table is most preferable.

(Properties of Catalyst)

Properties and size of these catalysts are not specifically limited. Specific examples of properties of the catalyst include powders, solid grinds, flakes, spherical molded articles, columnar molded articles and cylindrical molded articles. The size of the catalyst is preferably from 1 to 1000 μm in terms of an average particle size in case of a suspended bed or fluidized bed, and is from about 1 to 20 mm in case of a fixed bed.

In case of the suspended bed or fluidized bed, when the average particle size of the catalyst is smaller than the above range, it is difficult to separate the catalyst. On the other hand, when the particle size is larger than the above range, the reaction may not be efficiently carried out because of sedimentation of the catalyst. In case of the fixed bed, when the average particle size is smaller than the above range, clogging of a catalyst layer and an increase in differential pressure may occur. On the other hand, when the particle size is larger than the above range, the surface area of the catalyst per unit area of the reactor decreases thereby to lower the reaction efficiency, and therefore it is not preferable.

When the catalyst used in the method of the present invention (I) is a heterogeneous catalyst, those having properties and particle size suited for the reaction form can be selected and used.

The catalyst used in the method of the present invention (I) may be produced by any conventionally known method for producing a catalyst.

(Preferred Method for Producing Catalyst)

When the catalyst used in the method of the present invention (I) is a supported type catalyst comprising a carrier and a catalyst supported on the carrier, the catalyst is preferably produced by a method comprising the following steps in view of compatibility between high dispersion of the active site and reduction of cost required to produce the catalyst.

That is, the catalyst is preferably produced by the method comprising the following steps (A) and (B).

Step (A):

The step of preparing a solution containing a compound containing at least one element selected from the group consisting of elements of the group III, lanthanoid elements and actinoid elements of the Periodic Table dissolved in water or an organic solvent, and putting a carrier in the solution, thereby to impregnate the carrier with the solution Step (B):

The step of drying and firing the solid obtained in the step (A) to obtain a catalyst for production of 3-alkoxy-1-propanols The compound containing at least one element selected from the group consisting of elements of the group III, lanthanoid elements and actinoid elements of the Periodic Table used in the step (A) is not specifically limited as far as it is soluble in water or an organic solvent, but is preferably chloride, bromide, sulfate, carbonate, nitrate, phosphate, carbonate or alkoxide.

The method for producing a supported type catalyst comprising a carrier and a catalyst supported on the carrier used in the method of the present invention (I) is not specifically limited and the catalyst can be produced by a conventionally known method.

(Alcohol Compound)

The alcohol compound used to react with the allyl alcohol in the presence of a catalyst in the method of the present invention (I) is a compound having one or more hydroxyl groups in the structure. However, the subsequent is not limited to a hydroxyl group and the alcohol compound may have any substituent, in addition to the hydroxyl group.

Specific examples of the alcohol compound used in the present invention include, but are not limited, to methanol, ethanol, n-propanol, isopropanol, n-butanol, isobutanol, t-butanol, allyl alcohol, phenol, benzyl alcohol, ethylene glycol, 1,2-propanediol, 1,3-propanediol, 1,3-butanediol, 1,4-butanediol, 1,5-pentanediol, 1,6-hexanediol, glycerin, trimethylolpropane and pentaerythritol.

Among these alcohol compounds, methanol, ethanol, n-propanol, allyl alcohol, ethylene glycol and 1,3-propanediol are particularly preferable in view of an industrial value of the reaction product and availability.

(Reaction Form)

The reaction of the allyl alcohol and the alcohol compound in the present invention (I) can be carried out by bringing the allyl alcohol into contact with the alcohol compound in the presence of the catalyst. The reaction form may be any reaction form of a conventionally known reaction using an allyl alcohol, or a successive batch reaction used in the reaction using an alcohol compound, and any of a liquid phase method, a slurry method and a gas phase method may be used. As the catalyst, any of a homogeneous catalyst and a heterogeneous catalyst can be used. The form of the catalyst is not specifically limited and a suitable form can be selected according to the reaction form.

Specific examples of the reaction form used in the present invention include, but are not limited to, reaction forms such as simple stirring tank, bubble column type reaction tank and pipe type reaction tank in case of the homogeneous catalyst; and reaction forms such as suspended bed simple stirring tank, fluidized bed bubble column type reaction tank, fluidized bed pipe type reaction tank, fixed bed liquid phase circulating pipe type reaction tank, fixed bed trickle bed type pipe type reaction tank in case of the heterogeneous catalyst.

(Amount)

The amount of the catalyst used to react the allyl alcohol with the alcohol compound in the method for producing 3-alkoxy-1-propanols of the present invention (I) is not specifically limited because it varies depending on the reaction form. When the batch reaction is carried out, the amount of the catalyst is usually within a range from 0.001 to 20% by mass, preferably from 0.01 to 10% by mass, and more preferably from 0.1 to 5% by mass, based on a mixed solution of the allyl alcohol and the alcohol compound in case of the homogeneous catalyst, while the amount of the catalyst is usually within a range from 0.01 to 200% by mass, preferably from 0.1 to 100% by mass, and more preferably from 0.5 to 50% by mass, based on a mixed solution of the allyl alcohol and the alcohol compound in case of the heterogeneous catalyst.

When the amount of the catalyst is less than the above range, sufficient reaction rate suited for practical use may not be obtained. On the other hand, when the amount of the catalyst is more than the above range, a decrease in the reaction yield and an increase in the catalyst cost may be caused by an increase in the side reaction. Both cases are not preferable.

The amount of the allyl alcohol and the alcohol compound used in the method of the present invention (I) is not specifically limited. The allyl alcohol and the alcohol compound are usually used so that a ratio of the mass of the alcohol compound to that of the allyl alcohol is from 0.5 to 50. When the ratio of the mass of the alcohol compound to that of the allyl alcohol is less than 0.5, the reaction between allyl alcohols may occur and thus the objective reaction product of the allyl alcohol and the alcohol compound may not be produced with ease, and therefore it is not preferable. On the other hand, when the ratio of the mass of the alcohol compound to that of the allyl alcohol exceeds 50, a large amount of the unreacted alcohol compound must be removed in case of separating the objective product, resulting in high cost for industrial production, and therefore it is not preferable. The ratio of the mass of the alcohol compound to that of the allyl alcohol is preferably within a range from 1 to 30, and more preferably from 1 to 10.

(Reaction Conditions)

The reaction pressure in the reaction of the allyl alcohol and the alcohol compound in the method for producing 3-alkoxy-1-propanols of the present invention (I) is not specifically limited because it varies depending on the reaction temperature, the kind of the alcohol compound, and the mixing ratio of the allyl alcohol to the alcohol compound. The reaction can be carried out under normal pressure or applied pressure. In case the reaction is carried out at a temperature higher than the boiling point of either or both of the allyl alcohol and the alcohol compound, the reaction pressure is decided by the vapor pressure of either or both of them and the reaction can be carried out under applied pressure, in addition to the vapor pressure of the substrate, using an inert gas. Similarly, when the reaction is carried out at the temperature at which the vapor pressure is not produced in both the allyl alcohol and the alcohol compound, the reaction can be carried out under applied pressure using an inert gas. To enable the reaction to proceed efficiently, it is preferred to react under applied pressure as compared with reacting under normal pressure.

The reaction of the allyl alcohol and the alcohol compound in the method for producing 3-alkoxy-1-propanols of the present invention (I) can be carried out at any temperature as far as the reaction efficiency of the catalyst is not lowered. The reaction is usually carried out at a temperature within a range from 100 to 350° C., preferably from 130 to 300° C., and more preferably from 150 to 250° C. When the temperature is lower than 100° C., the reaction rate suited for practical use may not be obtained in the reaction of the allyl alcohol and the alcohol compound, and therefore it is not preferable. On the other hand, when the temperature exceeds 350° C., the isomerization reaction of the allyl alcohol may occur to produce undesired by-products derived from the allyl alcohol, and therefore it is not preferable.

(Presence of Water)

The reaction of the allyl alcohol and the alcohol compound in the method for producing 3-alkoxy-1-propanols of the present invention (I) can be carried out even if water is present in addition to the allyl alcohol and the alcohol compound. The amount of water used is not specifically limited. Even if the ratio of B (number of moles of water present in the reaction system) to A (number of moles of at least one element selected from the group consisting of elements of the group III, lanthanoid elements and actinoid elements of the Periodic Table contained in the catalyst, or total number of moles of plural elements, if any), (B/A), is 1, 5 or more, or 10 or more, the reaction of the allyl alcohol and the alcohol compound in the present invention (I) can be carried out.

This ratio (B/A) is preferably 50 or less, and more preferably 5 or less (particularly preferably 1 or less). When the ratio of the number of moles of water to that of the above elements, (B/A), exceeds 50, the reaction may not proceed smoothly because of reduced catalytic activity.

(Allyl Alcohol)

The allyl alcohol used in the method of the present invention (I) may be produced by any method.

Specific examples of the method for producing the allyl alcohol include, but are not limited to, a method for isomerization of propylene oxide, a method for hydrolysis of allyl chloride, and a method of producing allyl acetate from propylene and acetic acid and hydrolyzing the resulting allyl acetate.

The allyl alcohol in the method of the present invention (I) is preferably an allyl alcohol obtained by the method of producing allyl acetate from propylene and acetic acid and hydrolyzing the resulting allyl acetate among the above-mentioned methods because contamination with industrially undesired impurities, for example, a chlorine compound serving as a poisoning material of the reaction catalyst and an epoxy compound capable of producing by-products is prevented during the reaction with the alcohol compound.

(Conversion Ratio)

According to the above-mentioned method for producing 3-alkoxy-1-propanols of the present invention (I), when 3-methoxy-1-propanol is produced from the allyl alcohol and methanol, the conversion ratio of the allyl alcohol is 20% or more under preferable conditions and is 40% or more under more preferable conditions. As described in the later-mentioned Examples (Table 1), the selectivity coefficient of 3-methoxy-1-propanol is 60% or more under preferable conditions and is 70% or more (particularly preferably 75% or more) under more preferable conditions.

(Yield of Product)

In the present invention, the yield of the objective product (3-alkoxy-1-propanols) is preferably 0.5 or more, and more preferably 2.0 or more (particularly preferably 3.0 or more), per 1 mmol of metal used as the catalyst per one hour of the reaction time.

(Present Invention (II))

The present invention (II) will now be described. The present invention (II) is directed to 3-alkoxy-1-propanols produced by the method for producing 3-alkoxy-1-propanols of the present invention (I).

Since the method for producing 3-alkoxy-1-propanols of the present invention (I) involves reacting the allyl alcohol with the alcohol compound, the product 3-alkoxy-1-propanols substantially contain no carbonyl compound as impurities. Therefore, when 3-alkoxy-1-propanols of the present invention (II) are used as a material, 1,3-propanediol substantially containing no carbonyl compound as impurities can be produced. When a polyester is produced by using the resulting 1,3-propanediol, coloration and odor caused by the carbonyl compound can be suppressed.

(Confirmation of Carbonyl Compound)

The following procedures confirm whether or not 3-alkoxy-1-propanols contain the carbonyl compound.
1) Determination of known carbonyl compound due to gas chromatography, liquid chromatography and gas chromatography/mass spectrum
2) Confirmation of C=O stretching vibration peak at about 1600 to 1800 cm$^{-1}$ due to IR spectrum
3) Determination of solution of condensate of carbonyl compound and 2,4-dinitrophenylhydrazine due to visible light spectrum (ASTM E411-70)

(Present Invention (2-I))

First, the present invention (2-I) will be described. The present invention (2-I) is directed to a method for producing 1,3-propanediol, which comprises hydrolyzing an ether alcohol compound represented by the general formula (1) at a temperature of lower than 200° C. in the presence of at least one acid catalyst:

General Formula (1)

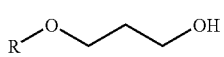
(Chemical Formula 3)

wherein R represents an alkyl group having 1 to 10 carbon atoms, a cycloalkyl group, or an aryl group, provided that R has no hydroxyl group.

(Catalyst)

The catalyst used in the method of the present invention (2-I) is an acid catalyst. Furthermore, the catalyst may be either Broensted acid or Lewis acid as far as it does not inhibit the hydrolysis reaction.

The catalyst used in the method of the present invention (2-I) is preferably mineral acid, inorganic solid acid, or sulfonic acid group-containing compound.

Mineral acids such as hydrochloric acid, nitric acid, sulfuric acid, phosphoric acid and boric acid can be used as the catalyst.

Among these mineral acids, nitric acid, sulfuric acid and phosphoric acid are preferable, and sulfuric acid and phosphoric acid are more preferable.

Inorganic solid acids such as zeolites, Nafion, activated clay and montmorillonite can be used as the catalyst.

Among these inorganic solid acids, zeolites and Nafion are preferable, and zeolites are more preferable.

Sulfonic acid group-containing compounds such as methanesulfonic acid, ethanesulfonic acid, propanesulfonic acid, butanesulfonic acid, trifluoromethanesulfonic acid, benzenesulfonic acid, p-toluenesulfonic acid, 2,4,6-trimethylbenzenesulfonic acid, hexylbenzenesulfonic acid, octylbenzenesulfonic acid, decylbenzenesulfonic acid, dodecylbenzenesulfonic acid, 1-naphthalenesulfonic acid and sulfonic acid type ion-exchange resin can be used as the catalyst.

Among these sulfonic acid group-containing compounds, methanesulfonic acid, trifluoromethanesulfonic acid, p-toluenesulfonic acid and dodecylbenzenesulfonic acid are preferable, and p-toluenesulfonic acid and dodecylbenzenesulfonic acid are more preferable.

(Form of Catalyst)

The form of the catalyst used in the method of the present invention (2-I) is not specifically limited and may be any of a homogeneous form and a heterogeneous form. The catalyst is preferably a heterogeneous catalyst in view of the operation for separation of the catalyst after the completion of the reaction, but may be a homogeneous catalyst.

Any homogeneous catalyst can be used as far as it is soluble during the reaction.

The homogeneous catalyst may be used for the reaction in the form of being dissolved previously in substrates such as ether alcohol compound and water, or may be used for the reaction by charging simultaneously with the substrate.

Any heterogeneous catalyst can be used as far as it is insoluble during the reaction. For example, there can also be used a so-called supported type catalyst comprising a carrier and a component supported on the carrier.

(Supported Type Catalyst)

When the catalyst used in the method of the present invention (2-I) is a supported type catalyst comprising a carrier and a catalyst supported on the carrier, usable carrier is not specifically limited as far as it does not react with the acid component and conventionally known carriers can be used. Specific examples of the carrier include activated carbon, silica, alumina, silica alumina, zeolite, titania, zirconia, magnesia and diatomaceous earth. In view of the influence on the reaction, the specific surface area during the production of the catalyst, or industrial utility such as strength of the carrier, silica, alumina and zeolite are preferable.

The surface area of the carrier which is used in the catalyst used in the method of the present invention (2-I) is preferably within a range from 50 to 4000 m$^2$/g, more preferably from 100 to 2000 m$^2$/g, and still more preferably from 200 to 1000 m$^2$/g.

When an acid component, as active species of the catalyst, is supported on the carrier, the amount of the acid component is preferably from 0.01 to 100% by mass based on the total mass of the carrier. When the amount of the acid component is less than 0.01% by mass, sufficient catalytic activity suited for practical use may not be obtained because of a low concentration of a catalytic active site, and therefore it is not preferable. On the other hand, when the amount exceeds 100% by mass, the effect of the carrier may not be exerted, and therefore it is not preferable.

The amount is more preferably within a range from 0.05 to 50% by mass, and still more preferably from 0.1 to 30% by mass.

When the catalyst used in the method of the present invention (2-I) is a supported type catalyst comprising a carrier and a catalyst supported on the carrier, for example, sulfonic acid-terminated surface hydroxyl group-modified silica, sulfonic acid-terminated surface hydroxyl group-modified alumina, phosphoric acid-terminated surface hydroxyl group-modified silica and phosphoric acid-terminated surface hydroxyl group-modified alumina can be used. These catalysts may be used alone or in combination.

When the catalyst used in the method of the present invention (2-I) is a heterogeneous catalyst, an inorganic solid acid catalyst is most preferable.

(Properties of Catalyst)

Properties and size of these catalysts are not specifically limited. Specific examples of properties of the catalyst include powders, solid grinds, flakes, spherical molded articles, columnar molded articles and cylindrical molded articles. The size of the catalyst is preferably from 1 to 1000 μm in terms of an average particle size in case of a suspended bed or fluidized bed, and is from about 1 to 20 mm in case of a fixed bed.

In case of the suspended bed or fluidized bed, when the average particle size of the catalyst is smaller than the above range, it is difficult to separate the catalyst. On the other hand, when the particle size is larger than the above range, the reaction may not be efficiently carried out because of sedimentation of the catalyst. In case of the fixed bed, when the average particle size is smaller than the above range, clogging of a catalyst layer and an increase in differential pressure may occur. On the other hand, when the particle size is larger than the above range, the surface area of the catalyst per unit area of the reactor decreases thereby to lower the reaction efficiency, and therefore it is not preferable.

When the catalyst used in the method of the present invention (2-I) is a heterogeneous catalyst, those having properties and particle size suited for the reaction form can be selected and used.

The catalyst used in the method of the present invention (2-I) may be produced by any conventionally known method for producing a catalyst.

(Preferred Method for Producing Catalyst)

In case the catalyst used in the method of the present invention (2-I) is a supported type catalyst comprising a carrier and a catalyst supported on the carrier, the catalyst is preferably produced by a method comprising the following steps in view of prevention of elimination of active species from the catalyst.

That is, the catalyst is preferably produced by the method comprising the following steps (A) and (B).

Step (A):

Step of adding a compound having both thiol and trimethoxysilyl groups in the structure and a carrier in an organic solvent and heating them, thereby to react the silanol and trimethoxysilyl groups on the surface of the carrier Step (B):

Step of washing the solid obtained in the step (A) and subjecting the solid to an oxidation treatment in an organic solvent, thereby to convert a thiol group into a sulfonic acid group, followed by washing and drying to obtain a catalyst for production of 1,3-propanediol As a matter of course, the method is not limited to these methods and the catalyst can be produced by a conventionally known method.

(Ether Alcohol Compound)

The ether alcohol compound represented by the general formula (1) in the method of the present invention (2-I) is a compound having one hydroxyl group and one ether structure in the structure.

Specific examples of the ether alcohol compound in the present invention include, but are not limited to, 3-methoxy-1-propanol, 3-ethoxy-1-propanol, 3-n-propoxy-1-propanol, 3-isopropoxy-1-propanol, 3-allyloxy-1-propanol, 3-n-butoxy-1-propanol, 3-t-butoxy-1-propanol, 3-pentyloxy-1-propanol, 3-hexyloxy-1-propanol, 3-phenoxy-1-propanol and 3-benzyloxy-1-propanol.

Among these ether alcohol compounds, 3-methoxy-1-propanol, 3-allyloxy-1-propanol and 3-benzyloxy-1-propanol are particularly preferable in view of ease of proceeding of the hydrolysis reaction.

(Hydrolysis Reaction)

The hydrolysis reaction of the ether alcohol compound in the present invention (2-I) can be carried out by bringing the ether alcohol compound into contact with water in the presence of a catalyst. The reaction form may be any reaction form of a successive batch reaction used in a conventionally known hydrolysis reaction. As the catalyst, any of a homogeneous catalyst and a heterogeneous catalyst can be used. The form of the catalyst is not specifically limited and a suitable form can be selected according to the reaction form.

Specific examples of the reaction form used in the present invention include, but are not limited to, reaction forms such as simple stirring tank, bubble column type reaction tank and pipe type reaction tank in case of the homogeneous catalyst; and reaction forms such as suspended bed simple stirring tank, fluidized bed bubble column type reaction tank, fluidized bed pipe type reaction tank, fixed bed liquid phase circulating pipe type reaction tank, fixed bed trickle bed type pipe type reaction tank in case of the heterogeneous catalyst.

(Amount)

The amount of the catalyst used in the hydrolysis reaction in the method for producing 1,3-propanediol of the present invention (2-I) is not specifically limited because it varies depending on the reaction form. When the batch reaction is carried out, the amount of the catalyst is usually within a range from 0.01 to 100% by mass, preferably from 0.1 to 50% by mass, and more preferably from 1 to 30% by mass, based on a mixed solution of the ether alcohol compound and water in case of the homogeneous catalyst, while the amount of the catalyst is usually within a range from 0.01 to 200% by mass, preferably from 0.1 to 150% by mass, and more preferably from 1 to 100% by mass, based on a mixed solution of the ether alcohol and water in case of the heterogeneous catalyst.

When the amount of the catalyst is less than the above range, sufficient reaction rate suited for practical use may not be obtained. On the other hand, when amount of the catalyst is more than the above range, a decrease in the reaction yield and an increase in the catalyst cost may be caused by an increase in the side reaction. Therefore, both cases are not preferable.

(Presence of Water)

The amount of the ether alcohol compound and water in the method of the present invention (2-I) is not specifically limited. In general, they can be used so that a ratio of the mass (B) of water to the mass (A) of the ether compound, (B/A), is within a range from 0.1 to 50. When the ratio of the mass of water to that of the ether compound is less than 0.1, the hydrolysis reaction may not occur smoothly and the objective 1,3-propanediol may not be produced with ease, and therefore it is not preferable. On the other hand, when the ratio of the mass of water to that of the ether compound exceeds 50, a large amount of water must be removed in case of separating the objective product, resulting in high cost for industrial production, and therefore it is not preferable. The ratio is preferably from 0.5 to 30, and more preferably from 1 to 20. In view of reduction of the cost for production of 1,3-propanediol, the ratio of the mass of water to that of the ether compound is preferably 5 or less (more preferably 3 or less).

(Reaction Conditions)

The reaction pressure in the hydrolysis reaction of the ether alcohol compound in the method for producing 1,3-propanediol of the present invention (2-I) is not specifically limited because it varies depending on the reaction temperature and the mixing ratio of the ether alcohol compound to water. The reaction can be carried out under normal pressure or applied pressure. In case the reaction is carried out at a temperature of higher than a boiling point of either or both of the ether alcohol compound and water, the reaction pressure is decided by a vapor pressure of either or both of them and the reaction can be carried out under applied pressure, in addition to the vapor pressure of the substrate, using an inert gas. Similarly, when the reaction is carried out at the temperature at which the vapor pressure is not produced in both the ether alcohol compound and water, the reaction can be carried out under applied pressure using an inert gas. To enable the reaction to proceed efficiently, it is preferred to react under applied pressure as compared with the case of reacting under normal pressure.

The reaction of the ether alcohol compound and water in the method for producing 1,3-propanediol of the present invention (2-I) can be carried out at any temperature as far as the reaction efficiency of the catalyst is not lowered, and the reaction is usually carried out at a temperature within a range from 50 to 200° C., preferably from 80 to 190° C., and more preferably from 100 to 180° C. When the temperature is lower than 50° C., the reaction rate suited for practical use may not be obtained in the reaction of the ether alcohol compound and water, and therefore it is not preferable. On the other hand, when the temperature exceeds 200° C., the isomerization reaction of the alcohol compound produced together with 1,3-propanediol by the hydrolysis reaction may occur to produce undesired by-products and, furthermore, by-products react with 1,3-propanediol to form secondary by-products, thereby lowering a selectivity coefficient of 1,3-propanediol, and therefore it is not preferable.

(Reaction Accelerator)

In the reaction of the ether alcohol compound and water in the method for producing 1,3-propanediol of the present invention (2-I), the reaction rate can be remarkably increased by adding reaction accelerators, in addition to the catalyst. The reaction accelerator is not specifically limited and is preferably iodide or bromide. Examples of preferable reaction accelerator include sodium iodide, potassium iodide, tetraethylammonium iodide, tetrabutylammonium iodide, hydrogen iodide, sodium bromide and potassium bromide. The amount of the reaction accelerator is usually within a range from 0.01 to 100% by mass, preferably from 0.1 to 50% by mass, and more preferably from I to 30% by mass, based on the mixed solution of the ether alcohol compound and water.

When the amount of the reaction accelerator is less than that of the mixed solution of the ether alcohol compound and water, sufficient acceleration effect suited for practical use may not be exerted. On the other hand, when the amount of the reaction accelerator is more than that of the mixed solution of the ether alcohol compound and water, corrosion of the reaction apparatus and increase in cost for removal of the reaction accelerator after use may occur. Therefore, both cases are not preferable.

(Method for Producing Ether Alcohol Compound)

The ether alcohol compound used in the method of the present invention (2-I) may be produced by any method.

Specific examples of the method for producing 3-alkoxy-1-propanol among the ether alcohol compound include, but are not limited to, a method of adding an alcohol compound to acrolein and hydrolyzing the mixture, a method of reacting an alkyl halide with 1,3-propanediol in the presence of metallic sodium or sodium hydroxide, a method of reacting 3-halogeno-1-propanol with an alcohol compound in the presence of metallic sodium or sodium hydroxide, and a method of reacting an allyl alcohol with an alcohol compound in the presence of a specific catalyst.

The ether alcohol compound in the method of the present invention (2-I) is preferably 3-alkoxy-1-propanol obtained by the method of reacting an allyl alcohol with an alcohol compound in the presence of a specific catalyst because contamination with industrially undesired impurities, for example, a chlorine compound serving as a poisoning material of the reaction catalyst and a carbonyl compound capable of producing by-products is prevented during the reaction.

According to the above-mentioned method for producing 1,3-propanediol of the present invention (2-I), when 1,3-propanediol is produced by hydrolyzing 3-methoxy-1-propanol, the conversion ratio of 3-methoxy-1-propanol is 50% or more under preferable conditions and Is 70% or more under more preferable conditions. A selectivity coefficient of 1,3-propanediol is 60% or more under preferable conditions and is 70% or more (particularly preferably 75% or more) under more preferable conditions.

(Present Invention (2-II))

The present invention (2-II) will now be described. The present invention (2-II) is directed to 1,3-propanediol produced by the method for producing 1,3-propanediol of the present invention (2-I).

Since the method for producing 1,3-propanediol of the present invention (2-I) is a method of hydrolyzing 3-alkoxy-1-propanols produced by reacting an allyl alcohol with an alcohol compound, the product 1,3-propanediol substantially contains no carbonyl compound as impurities. Therefore, when a polyester is produced by using the resulting 1,3-propanediol obtained by the present invention (2-II), coloration and odor caused by the carbonyl compound can be suppressed.

EXAMPLES

The present invention will be described in more detail by way of the following Examples and Comparative Examples, but the present invention is not limited thereto.

Analysis of the respective reactions in the Examples was carried out by gas chromatography (hereinafter abbreviated to "GC") under the following conditions.

Conditions for GC Analysis

GC-17A (manufactured by Shimadzu Corporation)

Column: TC-FFAP 0.25 mm$\phi$×30 m (manufactured by GL Science Co.)

Carrier: He 1 ml/min

Sprit ratio: 1/30

Detector: FID

Column temperature: 40° C. (10 min)→10° C./min→200° C. (40 min)

Injection temperature: 200° C.

Injection amount: 0.2 µl

Example 1

(Production of Activated Carbon-supported $La_2O_3$ Catalyst)

1.48 g of lanthanum nitrate hexahydrate (manufactured by Wako Pure Chemical Industries, Ltd.) was placed in a beaker and dissolved in 5.00 g of deionized water to obtain an aqueous solution (1). 5.00 g of activated carbon (manufactured by Mitsubishi Chemical Corporation, Diahope 008B, specific surface area: 1200 m$^2$/g) was added in the beaker in which the aqueous solution (1) was prepared so that the content of lanthanum oxide is 10% by mass based on activated carbon, thereby enabling the activated carbon to absorb the total amount of the aqueous solution (1).

The activated carbon which absorbed the aqueous solution (1) was dried at 110° C. in the presence of an air for 2 hours. Then, the activated carbon was oxidized at 400° C. in the presence of an air for 2 hours to obtain an activated carbon-supported lanthanum oxide catalyst.

Example 2

In a stainless steel autoclave having an inner volume of 120 ml (manufactured by Taiatsu Techno Corporation) equipped with a stirrer, 1.00 g of the activated carbon-supported lanthanum oxide catalyst produced in Example 1, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 3

(Production of Activated Carbon-supported $Pr_6O_{11}$ Catalyst)

1.44 g of praseodymium nitrate hexahydrate (manufactured by Wako Pure Chemical Industries, Ltd.) was placed in a beaker and dissolved in 4.00 g of deionized water to obtain an aqueous solution (2). 5.00 g of activated carbon (manufactured by Mitsubishi Chemical Corporation, Diahope 008B, specific surface area: 1200 m$^2$/g) was added in the beaker in which the aqueous solution (2) was prepared so that the content of praseodymium oxide is 10% by mass based on activated carbon, thereby enabling the activated carbon to absorb the total amount of the aqueous solution (2).

The activated carbon which absorbed the aqueous solution (2) was dried at 110° C. in the presence of an air for 2 hours. Then, the activated carbon was oxidized at 400° C. in the presence of an air for 2 hours to obtain an activated carbon-supported praseodymium oxide catalyst.

Example 4

In a stainless steel autoclave having an inner volume of 120 ml (manufactured by Taiatsu Techno Corporation) equipped with a stirrer, 1.00 g of the activated carbon-supported praseodymium oxide catalyst produced in Example 3, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 5

(Production of Activated Carbon-supported $Sm_2O_3$ catalyst)

1.42 g of samarium nitrate hexahydrate (manufactured by Wako Pure Chemical Industries, Ltd.) was placed in a beaker and dissolved in 4.00 g of deionized water to obtain an aqueous solution (3). 5.00 g of activated carbon (manufactured by Mitsubishi Chemical Corporation, Diahope 008B, specific surface area: 1200 m$^2$/g) was added in the beaker in which the aqueous solution (3) was prepared so that the content of samarium oxide is 10% by mass based on activated carbon, thereby enabling the activated carbon to absorb the total amount of the aqueous solution (3).

The activated carbon which absorbed the aqueous solution (3) was dried at 110° C. in the presence of an air for 2 hours. Then, the activated carbon was oxidized at 400° C. in the presence of an air for 2 hours to obtain an activated carbon-supported samarium oxide catalyst.

Example 6

In a stainless steel autoclave having an inner volume of 120 ml (manufactured by Taiatsu Techno Corporation) equipped with a stirrer, 1.00 g of the activated carbon-supported samarium oxide catalyst produced in Example 5, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 7

(Production of Activated Carbon-supported $Gd_2O_3$ Catalyst)

1.37 g of gadolinium nitrate hexahydrate (manufactured by Wako Pure Chemical Industries, Ltd.) was placed in a beaker and dissolved in 4.00 g of deionized water to obtain an aqueous solution (4). 5.00 g of activated carbon (manufactured by Mitsubishi Chemical Corporation, Diahope 008B, specific surface area: 1200 m$^2$/g) was added in the beaker in which the aqueous solution (4) was prepared so that the content of gadolinium oxide is 10% by mass based on activated carbon, thereby enabling the activated carbon to absorb the total amount of the aqueous solution (4).

The activated carbon which absorbed the aqueous solution (4) was dried at 110° C. in the presence of an air for 2 hours. Then, the activated carbon was oxidized at 400° C. in the presence of an air for 2 hours to obtain an activated carbon-supported gadolinium oxide catalyst.

Example 8

In a stainless steel autoclave having an inner volume of 120 ml (manufactured by Taiatsu Techno Corporation) equipped with a stirrer, 1.00 g of the activated carbon-supported gadolinium oxide catalyst produced in Example 7, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 9

(Production of Activated Carbon-supported Dy$_2$O$_3$ Catalyst)

1.39 g of dysprosium nitrate hexahydrate (manufactured by Wako Pure Chemical Industries, Ltd.) was placed in a beaker and dissolved in 4.00 g of deionized water to obtain an aqueous solution (5). 5.00 g of activated carbon (manufactured by Mitsubishi Chemical Corporation, Diahope 008B, specific surface area: 1200 m$^2$/g) was added in the beaker in which the aqueous solution (5) was prepared so that the content of dysprosium oxide is 10% by mass based on activated carbon, thereby enabling the activated carbon to absorb the total amount of the aqueous solution (5).

The activated carbon which absorbed the aqueous solution (5) was dried at 110° C. in the presence of an air for 2 hours. Then, the activated carbon was oxidized at 400° C. in the presence of an air for 2 hours to obtain an activated carbon-supported dysprosium oxide catalyst.

Example 10

In a stainless steel autoclave having an inner volume of 120 ml (manufactured by Taiatsu Techno Corporation) equipped with a stirrer, 1.00 g of the activated carbon-supported dysprosium oxide catalyst produced in Example 9, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 11

(Production of Activated Carbon-supported Ho$_2$O$_3$ Catalyst)

1.36 g of holmium nitrate hexahydrate (manufactured by Wako Pure Chemical Industries, Ltd.) was placed in a beaker and dissolved in 4.00 g of deionized water to obtain an aqueous solution (6). 4.00 g of activated carbon (manufactured by Mitsubishi Chemical Corporation, Diahope 008B, specific surface area: 1200 m$^2$/g) was added in the beaker in which the aqueous solution (6) was prepared so that the content of holmium oxide is 10% by mass based on activated carbon, thereby enabling the activated carbon to absorb the total amount of the aqueous solution (6).

The activated carbon which absorbed the aqueous solution (6) was dried at 110° C. in the presence of an air for 2 hours. Then, the activated carbon was oxidized at 400° C. in the presence of an air for 2 hours to obtain an activated carbon-supported holmium oxide catalyst.

Example 12

In a stainless steel autoclave having an inner volume of 120 ml (manufactured by Taiatsu Techno Corporation) equipped with a stirrer, 1.00 g of the activated carbon-supported holmium oxide catalyst produced in Example 11, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 13

(Production of Activated Carbon-supported Er$_2$O$_3$ Catalyst)

1.37 g of erbium nitrate hexahydrate (manufactured by Wako Pure Chemical Industries, Ltd.) was placed in a beaker and dissolved in 4.00 g of deionized water to obtain an aqueous solution (7). 5.00 g of activated carbon (manufactured by Mitsubishi Chemical Corporation, Diahope 008B, specific surface area: 1200 m$^2$/g) was added in the beaker in which the aqueous solution (7) was prepared so that the content of erbium oxide is 10% by mass based on activated carbon, thereby enabling the activated carbon to absorb the total amount of the aqueous solution (7).

The activated carbon which absorbed the aqueous solution (7) was dried at 110° C. in the presence of an air for 2 hours. Then, the activated carbon was oxidized at 400° C. in the presence of an air for 2 hours to obtain an activated carbon-supported erbium oxide catalyst.

Example 14

In a stainless steel autoclave having an inner volume of 120 ml (manufactured by Taiatsu Techno Corporation) equipped with a stirrer, 1.00 g of the activated carbon-supported erbium oxide catalyst produced in Example 13, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 15

(Production of Activated Carbon-supported $Yb_2O_3$ Catalyst)

1.22 g of ytterbium nitrate tetrahydrate (manufactured by Wako Pure Chemical Industries, Ltd.) was placed in a beaker and dissolved in 4.00 g of deionized water to obtain an aqueous solution (8). 5.00 g of activated carbon (manufactured by Mitsubishi Chemical Corporation, Diahope 008B, specific surface area: 1200 $m^2/g$) was added in the beaker in which the aqueous solution (8) was prepared so that the content of ytterbium oxide is 10% by mass based on activated carbon, thereby enabling the activated carbon to absorb the total amount of the aqueous solution (8).

The activated carbon which absorbed the aqueous solution (8) was dried at 110° C. in the presence of an air for 2 hours. Then, the activated carbon was oxidized at 400° C. in the presence of an air for 2 hours to obtain an activated carbon-supported ytterbium oxide catalyst.

Example 16

In a stainless steel autoclave having an inner volume of 120 ml (manufactured by Taiatsu Techno Corporation) equipped with a stirrer, 1.00 g of the activated carbon-supported ytterbium oxide catalyst produced in Example 15, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 17

(Production of Activated Carbon-supported $Y_2O_3$ Catalyst)

1.88 g of yttrium nitrate hexahydrate (manufactured by Kanto Kagaku) was placed in a beaker and dissolved in 4.00 g of deionized water to obtain an aqueous solution (9). 5.00 g of activated carbon (manufactured by Mitsubishi Chemical Corporation, Diahope 008B, specific surface area: 1200 $m^2/g$) was added in the beaker in which the aqueous solution (9) was prepared so that the content of yttrium oxide is 10% by mass based on activated carbon, thereby enabling the activated carbon to absorb the total amount of the aqueous solution (9).

The activated carbon which absorbed the aqueous solution (9) was dried at 110° C. in the presence of an air for 2 hours. Then, the activated carbon was oxidized at 400° C. in the presence of an air for 2 hours to obtain an activated carbon-supported yttrium oxide catalyst.

Example 18

In a stainless steel autoclave having an inner volume of 120 ml (manufactured by Taiatsu Techno Corporation) equipped with a stirrer, 1.00 g of the activated carbon-supported yttrium oxide catalyst produced in Example 17, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 19

(Production of Activated Carbon-supported $Y_2O_3$ catalyst)

1.86 g of yttrium nitrate hexahydrate (manufactured by Kanto Kagaku) was placed in a beaker and dissolved in 4.00 g of deionized water to obtain an aqueous solution (10). 5.00 g of activated carbon (manufactured by TSURUMICOAL CO., LTD., HC-20CS, specific surface area: 1855 $m^2/g$) was added in the beaker in which the aqueous solution (10) was prepared so that the content of yttrium oxide is 10% by mass based on activated carbon, thereby enabling the activated carbon to absorb the total amount of the aqueous solution (10).

The activated carbon which absorbed the aqueous solution (10) was dried at 110° C. in the presence of an air for 2 hours. Then, the activated carbon was oxidized at 400° C. in the presence of an air for 2 hours to obtain an activated carbon-supported yttrium oxide catalyst.

Example 20

In a stainless steel autoclave having an inner volume of 120 ml (manufactured by Taiatsu Techno Corporation) equipped with a stirrer, 1.00 g of the activated carbon-supported yttrium oxide catalyst produced in Example 19, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 5 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example)

Example 21

(Production of Activated Carbon-supported $Y_2O_3$ Catalyst)

1.86 g of yttrium nitrate hexahydrate (manufactured by Kanto Kagaku) was placed in a beaker and dissolved in 4.00 g of deionized water to obtain an aqueous solution (11). 5.00 g of activated carbon (manufactured by TSURUMICOAL CO., LTD., HC-20CS, specific surface area: 1855 m²/g) fired previously at 110° C. for 2 hours was added in the beaker in which the aqueous solution (11) was prepared so that the content of yttrium oxide is 10% by mass based on activated carbon, thereby enabling the activated carbon to absorb the total amount of the aqueous solution (11).

The activated carbon which absorbed the aqueous solution (11) was dried at 110° C. in the presence of an air for 2 hours. Then, the activated carbon was oxidized at 400° C. in the presence of an air for 2 hours to obtain an activated carbon-supported yttrium oxide catalyst.

Example 22

In a stainless steel autoclave having an inner volume of 120 ml (manufactured by Taiatsu Techno Corporation) equipped with a stirrer, 1.00 g of the activated carbon-supported yttrium oxide catalyst produced in Example 21, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 5 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 23

In a stainless steel autoclave having an inner volume of 120 ml (manufactured by Taiatsu Techno Corporation) equipped with a stirrer, 1.00 g of the activated carbon-supported yttrium oxide catalyst produced in Example 17, 30.00 g of methanol, 4.50 g of allyl alcohol and 0.50 g of deionized water were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 24

(Production of Activated Carbon-supported $Sc_2O_3$ Catalyst)

2.30 g of scandium nitrate trihydrate (manufactured by AVOCADO Co.) was placed in a beaker and dissolved in 4.00 g of deionized water to obtain an aqueous solution (12). 5.00 g of activated carbon (manufactured by Mitsubishi Chemical Corporation, Diahope 008B, specific surface area: 1200 m²/g) was added in the beaker in which the aqueous solution (12) was prepared so that the content of scandium oxide is 10% by mass based on activated carbon, thereby enabling the activated carbon to absorb the total amount of the aqueous solution (12).

The activated carbon which absorbed the aqueous solution (12) was dried at 110° C. in the presence of an air for 2 hours. Then, the activated carbon was oxidized at 400° C. in the presence of an air for 2 hours to obtain an activated carbon-supported scandium oxide catalyst.

Example 25

In a stainless steel autoclave having an inner volume of 120 ml (manufactured by Taiatsu Techno Corporation) equipped with a stirrer, 1.00 g of the activated carbon-supported scandium oxide catalyst produced in Example 24, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 3 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 26

In a stainless steel autoclave having an inner volume of 120 ml (manufactured by Taiatsu Techno Corporation) equipped with a stirrer, 1.00 g of the activated carbon-supported scandium oxide catalyst produced in Example 24, 30.00 g of methanol, 4.50 g of allyl alcohol and 0.50 g of deionized water were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 27

In a stainless steel autoclave having an inner volume of 30 ml (manufactured by Taiatsu Techno Corporation) including a stirrer, 0.20 g of the activated carbon-supported yttrium oxide catalyst produced in Example 17 and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 200° C. for 5 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Example 28

In a stainless steel autoclave having an inner volume of 30 ml (manufactured by Taiatsu Techno Corporation) including a stirrer, 0.20 g of the activated carbon-supported scandium oxide catalyst produced in Example 24 and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 200° C. for 5 hours.

After the completion of the reaction, the vessel was cooled to room temperature and depressurized. After opening a reactor, the supernatant was sampled and analyzed by GC.

The results calculated by GC chromatogram are shown in Table 1 described hereinafter. GC revealed that peaks assigned to carbonyl compounds such as 3-methoxy-1-propionaldehyde and 3-allyloxy-1-propionaldehyde were not detected (these carbonyl compounds showed GC detection limit of 10 ppm or less in this example).

Comparative Example 1

In a stainless steel autoclave having an inner volume of 120 ml (manufactured by Taiatsu Techno Corporation) equipped with a stirrer, 1.00 g of a magnesium oxide catalyst (manufactured by Wako Pure Chemical Industries, Ltd., 0.01 pm), 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter.

Comparative Example 2

3.54 g of magnesium nitrate hexahydrate (manufactured by Wako Pure Chemical Industries, Ltd.) was placed in a beaker and dissolved in 4.00 g of deionized water to obtain an aqueous solution (13). 5.00 g of activated carbon (manufactured by Mitsubishi Chemical Corporation, Diahope 008B, specific surface area: 1200 m$^2$/g) was added in the beaker in which the aqueous solution (13) was prepared so that the content of magnesium oxide is 10% by mass based on activated carbon, thereby enabling the activated carbon to absorb the total amount of the aqueous solution (13).

The activated carbon which absorbed the aqueous solution (13) was dried at 110° C. in the presence of an air for 2 hours. Then, the activated carbon was oxidized at 400° C. in the presence of an air for 2 hours to obtain an activated carbon-supported magnesium oxide catalyst.

In a stainless steel autoclave having an inner volume of 120 ml (manufactured by Taiatsu Techno Corporation) equipped with a stirrer, 1.00 g of this catalyst, 30.00 g of methanol and 5.00 g of allyl alcohol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm with a magnetic stirrer and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 described hereinafter.

Comparative Example 3

In a stainless steel autoclave having an inner volume of 120 ml (manufactured by Taiatsu Techno Corporation) equipped with a stirrer, 1.00 g of a magnesium oxide catalyst (manufactured by Wako Pure Chemical Industries, Ltd., 0.01 μm), 30.00 g of methanol, 4.50 g of allyl alcohol and 0.50 g of deionized water were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring at 800 rpm with a magnetic stirrer and then reacted at 200° C. for 6 hours.

After the completion of the reaction, the vessel was cooled to room temperature and depressurized. After opening a reactor, the supernatant was sampled and analyzed by GC.

The results calculated by GC chromatogram are shown in Table 1 below.

(Table 1)

TABLE 1

Reaction of allyl alcohol (AAL) and alcohol by various catalysts

| | Catalyst | Catalyst (g) | Kind of alcohol | Reaction temperature (° C.) | Reaction time (hr) | Conversion ratio of AAL (%) | Selectivity coefficient 3-MP[a] (%) | Selectivity coefficient 3-AP[a] (%) | Yield of 3-MP per 1 mmol of metal per one hour (%/mmol · hr) |
|---|---|---|---|---|---|---|---|---|---|
| Examples | | | | | | | | | |
| 2 | La$_2$O$_3$-activated carbon | | Methanol | 200 | 6 | 20.5 | 41.5 | 6.0 | 2.31 |
| 4 | Pr$_6$O$_{11}$-activated carbon | 1.0 | Methanol | 200 | 3 | 7.4 | 64.2 | 10.2 | 2.74 |
| 6 | Sm$_2$O$_3$-activated carbon | 1.0 | Methanol | 200 | 6 | 14.3 | 68.7 | 9.6 | 2.86 |
| 8 | Gd$_2$O$_3$-activated carbon | 1.0 | Methanol | 200 | 3 | 7.0 | 65.1 | 8.8 | 2.75 |
| 10 | Dy$_2$O$_3$-activated carbon | 1.0 | Methanol | 200 | 3 | 7.2 | 68.8 | 8.6 | 3.08 |
| 12 | Ho$_2$O$_3$-activated carbon | 1.0 | Methanol | 200 | 3 | 7.1 | 68.9 | 8.8 | 3.08 |
| 14 | Er$_2$O$_3$-activated carbon | 1.0 | Methanol | 200 | 3 | 7.4 | 70.2 | 8.7 | 3.31 |
| 16 | Yb$_2$O$_3$-activated carbon | 1.0 | Methanol | 200 | 6 | 15.9 | 73.2 | 9.0 | 3.82 |
| 18 | Y$_2$O$_3$-activated carbon | 1.0 | Methanol | 200 | 6 | 19.2 | 73.9 | 8.6 | 2.67 |
| 20 | Y$_2$O$_3$-activated carbon[b] | 1.0 | Methanol | 200 | 5 | 21.5 | 72.9 | 7.3 | 3.54 |
| 22 | Y$_2$O$_3$-activated carbon[c] | 1.0 | Methanol | 200 | 5 | 26.1 | 77.4 | 7.4 | 4.56 |
| 23 | Y$_2$O$_3$-activated carbon | 1.0 | Methanol[d] | 200 | 6 | 6.4 | 68.5 | 7.7 | 0.82 |
| 25 | Sc$_2$O$_3$-activated carbon | 1.0 | Methanol | 200 | 3 | 12.5 | 72.2 | 8.7 | 2.07 |
| 26 | Sc$_2$O$_3$-activated carbon | 1.0 | Methanol[d] | 200 | 6 | 13.3 | 74.8 | 8.4 | 1.14 |
| 27 | Y$_2$O$_3$-activated carbon | 0.2 | — | 200 | 5 | 16.2 | — | 70.1 | — |
| 28 | Sc$_2$O$_3$-activated carbon | 0.2 | — | 200 | 5 | 14.5 | — | 68.0 | — |
| Comparative Examples | | | | | | | | | |
| 1 | MgO | 1.0 | Methanol | 200 | 6 | 6.1 | 85.4 | 6.0 | 0.035 |
| 2 | MgO-activated carbon | 1.0 | Methanol | 200 | 6 | 3.9 | 75.5 | 7.8 | 0.20 |
| 3 | MgO | 1.0 | Methanol[d] | 200 | 6 | 2.3 | 63.9 | 5.9 | 0.010 |

[a]3-MP: 3-methoxy-1-propanol, 3-AP: 3-allyloxy-1-propanol
[b]Activated carbon having a specific surface area of 1855 m$^2$/g is used, activated carbon having a specific surface area of 1200 m$^2$/g is used, except for Examples 20 and 22
[c]Activated carbon having a specific surface area of 1855 m$^2$/g is fired at 110° C. for 2 hours before a suporting treatment
[d]Allyl alcohol containing 10% by mass of water is used

Example 2-1

In a stainless steel autoclave having an inner volume of 30 ml (manufactured by Taiatsu Techno Corporation, in Teflon pestle) including a stirrer, 0.10 g of sulfuric acid, 6.00 g of deionized water and 0.30 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-2

In a stainless steel autoclave having an inner volume of 30 ml (manufactured by Taiatsu Techno Corporation, in Teflon pestle) including a stirrer, 0.10 g of sulfuric acid, 6.00 g of deionized water and 1.20 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-3

In a stainless steel autoclave having an inner volume of 30 ml (manufactured by Taiatsu Techno Corporation, in Teflon pestle) including a stirrer, 0.30 g of methanesulfonic acid, 6.00 g of deionized water and 0.30 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-4

In a stainless steel autoclave having an inner volume of 30 ml (manufactured by Taiatsu Techno Corporation, in Teflon pestle) including a stirrer, 0.30 g of p-toluenesulfonic acid, 6.00 g of deionized water and 0.30 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-5

In a stainless steel autoclave having an inner volume of 30 ml (manufactured by Taiatsu Techno Corporation, in Teflon pestle) including a stirrer, 0.30 g of p-toluenesulfonic acid, 6.00 g of deionized water and 1.20 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-6

In a stainless steel autoclave having an inner volume of 30 ml (manufactured by Taiatsu Techno Corporation, in Teflon pestle) including a stirrer, 0.30 g of dodecylbenzenesulfonic acid, 6.00 g of deionized water and 0.60 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-7

In a stainless steel autoclave having an inner volume of 30 ml (manufactured by Taiatsu Techno Corporation, in Teflon pestle) including a stirrer, 0.30 g of dodecylbenzenesulfonic acid, 6.00 g of deionized water and 1.20 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 190° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-8

In a stainless steel autoclave having an inner volume of 30 ml (manufactured by Taiatsu Techno Corporation, in Teflon pestle) including a stirrer, 0.10 g of sulfuric acid, 0.03 g of potassium iodide, 5.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 6 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-9

In a stainless steel autoclave having an inner volume of 30 ml (manufactured by Taiatsu Techno Corporation, in Teflon pestle) including a stirrer, 0.10 g of sulfuric acid, 0.40 g of tetrabutylammonium iodide, 5.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 6 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-10

In a stainless steel autoclave having an inner volume of 30 ml (manufactured by Taiatsu Techno Corporation, in Teflon pestle) including a stirrer, 1.42 g of hydriodic acid, 5.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 120° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-11

In a stainless steel autoclave having an inner volume of 30 ml (manufactured by Taiatsu Techno Corporation, in Teflon pestle) including a stirrer, 0.10 g of sulfuric acid, 0.13 g of potassium bromide, 5.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-12

In a stainless steel autoclave having an inner volume of 30 ml (manufactured by Taiatsu Techno Corporation, in Teflon pestle) including a stirrer, 0.10 g of sulfuric acid, 0.18 g of potassium iodide, 3.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 150° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as 3-methoxy-1-propionaldehyde and 3-hydroxy-1-propionaldehyde were not detected (these carbonyl compounds showed GC detection limit of 10 ppm or less in this example).

Example 2-13

In a stainless steel autoclave having an inner volume of 30 ml (manufactured by Taiatsu Techno Corporation, in Teflon pestle) including a stirrer, 0.06 g of sulfuric acid, 3.90 g of deionized water and 1.30 g of 3-allyloxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 3 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example).

Example 2-14

In a stainless steel autoclave having an inner volume of 30 ml (manufactured by Taiatsu Techno Corporation, in Teflon pestle) including a stirrer, 0.50 g of β type zeolite (manufactured by Zeolist Co., Si/Al=75), 3.90 g of deionized water and 1.30 g of 3-allyloxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 3 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example).

Example 2-15

In a stainless steel autoclave having an inner volume of 30 ml (manufactured by Taiatsu Techno Corporation, in Teflon pestle) including a stirrer, 0.50 g of H-ZSM-5 (Si/Al=25), 3.90 g of deionized water and 1.30 g of 3-allyloxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for one hour.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example).

Comparative Example 2-1

In a stainless steel autoclave having an inner volume of 30 ml (manufactured by Taiatsu Techno Corporation, in Teflon pestle) including a stirrer, 0.10 g of sulfuric acid, 5.00 g of deionized water and 1.00 g of 3-methoxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 220° C. for 10 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example), but 1,3-dimethoxypropane was produced.

Comparative Example 2-2

In a stainless steel autoclave having an inner volume of 30 ml (manufactured by Taiatsu Techno Corporation, in Teflon pestle) including a stirrer, 0.10 g of sulfuric acid, 6.50 g of deionized water and 1.30 g of 3-allyloxy-1-propanol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 220° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example), but diallyl ether and 1,3-diallyloxypropane were produced.

Comparative Example 2-3

In a stainless steel autoclave having an inner volume of 30 ml (manufactured by Taiatsu Techno Corporation, in Teflon pestle) including a stirrer, 0.10 g of sulfuric acid, 5.00 g of deionized water and 1.00 g of 4-oxa-1,7-heptanediol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example).

Comparative Example 2-4

In a stainless steel autoclave having an inner volume of 30 ml (manufactured by Taiatsu Techno Corporation, in Teflon pestle) including a stirrer, 0.50 g of H-ZSM-5(Si/Al =25), 5.00 g of deionized water and 1.00 g of 4-oxa-1,7-heptanediol were charged, and then an apparatus was assembled. After closing a vessel, an air in the autoclave was replaced with nitrogen by repeating an operation of pressurizing the autoclave to 1.0 MPa (gauge pressure) with nitrogen and depressurizing to 0.0 MPa (gauge pressure) five times. The contents were heated while stirring with a magnetic stirrer and then reacted at 180° C. for 5 hours.

After the completion of the reaction, the vessel was cooled to room temperature and depressurized. After opening a reactor, the supernatant was sampled and analyzed by GC.

The results calculated by GC chromatogram are shown in Table 2-1 described hereinafter.

GC revealed that peaks assigned to carbonyl compounds such as acrolein, 3-allyloxy-1-propionaldehyde and 3-hydroxy-1-propionaldehyde were not detected (these carbonyl compounds showed GC detection limit of 10 ppm or less in this example).

TABLE 2-1

Table 2-1: Hydrolysis of ether alcohol compound by acid catalyst

| | Acid catalyst | Amount of catalyst (g) | Reaction auxiliary | Substrate | Amount of substrate (g) | H₂O/substrate (mass ratio) | Reaction temperature (° C.) | Reaction time (hr) | Conversion ratio (%) | Selectivity coefficient of 1,3-propanediol (%) |
|---|---|---|---|---|---|---|---|---|---|---|
| Examples | | | | | | | | | | |
| 2-1 | H₂SO₄ | 0.1 | — | 3-MP⁽ᵉ⁾ | 0.3 | 20 | 190 | 10 | 74.5 | 76.3 |
| 2-2 | H₂SO₄ | 0.1 | — | 3-MP⁽ᵉ⁾ | 1.2 | 5 | 190 | 10 | 68.2 | 68.6 |
| 2-3 | MS⁽ᵃ⁾ | 0.3 | — | 3-MP⁽ᵉ⁾ | 0.3 | 20 | 190 | 5 | 84.5 | 67.6 |
| 2-4 | PTS⁽ᵇ⁾ | 0.3 | — | 3-MP⁽ᵉ⁾ | 0.3 | 20 | 180 | 10 | 67.4 | 70.9 |
| 2-5 | PTS⁽ᵇ⁾ | 0.3 | — | 3-MP⁽ᵉ⁾ | 1.2 | 5 | 190 | 10 | 77.3 | 62.8 |
| 2-6 | DBS⁽ᶜ⁾ | 0.3 | — | 3-MP⁽ᵉ⁾ | 0.6 | 10 | 190 | 10 | 73.8 | 76.6 |
| 2-7 | DBS⁽ᶜ⁾ | 0.3 | — | 3-MP⁽ᵉ⁾ | 1.2 | 5 | 190 | 10 | 68.8 | 68.0 |
| 2-8 | H₂SO₄ | 0.1 | KI | 3-MP⁽ᵉ⁾ | 1.0 | 5 | 180 | 6 | 51.8 | 76.2 |
| 2-9 | H₂SO₄ | 0.1 | TBAI⁽ᵈ⁾ | 3-MP⁽ᵉ⁾ | 1.0 | 5 | 180 | 6 | 71.8 | 77.0 |
| 2-10 | HI | 1.42 | — | 3-MP⁽ᵉ⁾ | 1.0 | 5 | 120 | 5 | 64.0 | 78.9 |
| 2-11 | H₂SO₄ | 0.1 | KBr | 3-MP⁽ᵉ⁾ | 1.0 | 5 | 180 | 5 | 74.3 | 69.1 |
| 2-12 | H₂SO₄ | 0.1 | KI | 3-MP⁽ᵉ⁾ | 1.0 | 3 | 150 | 5 | 55.3 | 69.8 |
| 2-13 | H₂SO₄ | 0.06 | — | 3-AP⁽ᶠ⁾ | 1.3 | 3 | 180 | 3 | 60.1 | 74.8 |
| 2-14 | β-zeolite | 0.5 | — | 3-AP⁽ᶠ⁾ | 1.3 | 3 | 180 | 3 | 62.4 | 75.1 |
| 2-15 | H-ZSM-5 | 0.5 | — | 3-AP⁽ᶠ⁾ | 1.3 | 3 | 180 | 1 | 49.5 | 84.3 |
| Comparative Examples | | | | | | | | | | |
| 2-1 | H₂SO₄ | 0.1 | — | 3-MP⁽ᵉ⁾ | 1.0 | 5 | 220 | 10 | 77.5 | 36.2 |
| 2-2 | H₂SO₄ | 0.1 | — | 3-AP⁽ᶠ⁾ | 1.3 | 5 | 200 | 5 | 82.3 | 34.7 |
| 2-3 | H₂SO₄ | 0.1 | — | 4-O-1,7-HD⁽ᵍ⁾ | 1.0 | 5 | 180 | 5 | 24.9 | 91.8 |
| 2-4 | H-ZSM-5 | 0.5 | — | 4-O-1,7-HD⁽ᵍ⁾ | 1.0 | 5 | 180 | 5 | 25.5 | 72.8 |

⁽ᵃ⁾MS: Methanesulfonic acid
⁽ᵇ⁾PTS: p-toluenesulfonic acid
⁽ᶜ⁾DBS: Dodecylbenzenesulfonic acid
⁽ᵈ⁾TBAI: Tetrabutylammonium iodide
⁽ᵉ⁾3-MP: 3-methoxy-1-propanol
⁽ᶠ⁾3-AP: 3-allyloxy-1-propanol
⁽ᵍ⁾4-O-1,7-HD: 4-oxa-1,7-heptanediol

INDUSTRIAL APPLICABILITY

As described above, according to the method for producing 3-alkoxy-1-propanols of the present invention, 3-alkoxy-1-propanols having a very small content of carbonyl impurities can be produced with high efficiency.

Therefore, 3-alkoxy-1-propanols obtained by the method for 3-alkoxy-1-propanols of the present invention have high purity as compared with 3-alkoxy-1-propanols obtained by a conventional method, and 1,3-propanediol substantially containing no carbonyl compound as impurities can be produced by using 3-alkoxy-1-propanols as a material.

According to the method for producing 1,3-propanediol of the present invention, 1,3-propanediol having a very small content of carbonyl impurities can be produced with high efficiency.

Also 1,3-propanediol obtained by the method for producing 1,3-propanediol of the present invention has high purity as compared with 1,3-propanediol obtained by a conventional method and it is apparent that a resin with less odor and coloration can be produced at a low cost by using the resulting 1,3-propanediol as a material of a resin such as polyester.

The invention claimed is:

1. A method for producing 1,3-propanediol, which comprises:

reacting an allyl alcohol with an alcohol compound in the presence of a catalyst containing at least one element selected from the group consisting of scandium, yttrium, and lanthanoid elements of the Periodic Table, to thereby obtain 3-alkoxy-1-propanol, and hydrolyzing the 3-alkoxy-1-propanol at a temperature of lower than 200° C. in the presence of at least one acid catalyst.

2. A method for producing 3-alkoxy-1-propanol, which comprises reacting an allyl alcohol with an alcohol compound in the presence of a catalyst containing at least one element selected from the group consisting of scandium, yttrium, and lanthanoid elements of the Periodic Table.

3. The method for producing 3-alkoxy-1-propanol according to claim 2, wherein the catalyst containing at least one element selected from the group consisting of scandium, yttrium, and lanthanoid elements of the Periodic Table is an oxide.

4. The method for producing 3-alkoxy-1-propanol according to claim 2, wherein the catalyst containing at least one element selected from the group consisting of scandium, yttrium, and lanthanoid elements of the Periodic Table is selected from the group consisting of scandium oxide, yttrium oxide, lanthanum oxide, samarium oxide, ytterbium oxide, neodymium oxide and lutetium oxide.

5. The method for producing 3-alkoxy-1-propanol according to claim 2, wherein the catalyst containing at least one element selected from the group consisting of scandium, yttrium, and lanthanoid elements of the Periodic Table is an alkoxide compound.

6. The method for producing 3-alkoxy-1-propanol according to claim 5, wherein the catalyst containing at least one element selected from the group consisting of scandium, yttrium, and lanthanoid elements of the Periodic Table is selected from the group consisting of scandium trimethoxide, scandium triethoxide, scandium triisopropoxide, yttrium trimethoxide, yttrium triethoxide, yttrium triisopropoxide, ytterbium trimethoxide, ytterbium triethoxide and ytterbium triisopropoxide.

7. The method for producing 3-alkoxy-1-propanol according to claim 2, wherein the catalyst containing at least one element selected from the group consisting of scandium, yttrium, and lanthanoid elements of the Periodic Table is supported on a carrier.

8. The method for producing 3-alkoxy-1-propanol according to claim 7, wherein the carrier is either activated carbon or magnesia.

9. The method for producing 3-alkoxy-1-propanol according to claim 8, wherein a specific surface area of the carrier is 1000 m2/g or more.

10. The method for producing 3-alkoxy-1-propanol according to claim 2, wherein the alcohol compound to be reacted with the allyl alcohol is at least one selected from the group consisting of methanol, ethanol, n-propanol, isopropanol, n-butanol, isobutanol, t-butanol, and allyl alcohol.

11. The method for producing 3-alkoxy-1-propanol according to claim 2, wherein the reaction of the allyl alcohol and the alcohol compound is carried out in the presence of water.

12. The method for producing 3-alkoxy-1-propanol according to claim 11, wherein the amount of water present in the reaction system is not less than the number of moles of elements in the catalyst containing at least one element selected from the group consisting of scandium, yttrium, and lanthanoid elements of the Periodic Table.

13. The method for producing 3-alkoxy-1-propanol according to claim 2, wherein the yield of 3-alkoxy-l-propanol is 0.5 or more per 1 mmol of metal used as the catalyst per one hour of the reaction time.

* * * * *